United States Patent [19]
Bitton et al.

[11] Patent Number: 5,633,144
[45] Date of Patent: *May 27, 1997

[54] ASSAY PAD AND METHOD FOR DETERMINATION OF THE PRESENCE OF TOTAL COLIFORMS

[75] Inventors: Gabriel Bitton; Ben Koopman, both of Gainesville, Fla.

[73] Assignee: University of Florida Research Foundation, Inc., Gainesville, Fla.

[*] Notice: The term of this patent shall not extend beyond the expiration date of Pat. No. 5,149,656.

[21] Appl. No.: 277,126

[22] Filed: Jul. 19, 1994

Related U.S. Application Data

[63] Continuation of Ser. No. 188,343, Jan. 27, 1994, abandoned, which is a continuation of Ser. No. 946,973, Sep. 17, 1992, abandoned, which is a continuation-in-part of Ser. No. 518,686, May 3, 1990, Pat. No. 5,149,656.

[51] Int. Cl.$^6$ ..................................... C12Q 1/10
[52] U.S. Cl. ........................ 435/38; 435/34; 435/287.7
[58] Field of Search ............................. 435/14, 34, 38, 435/288

[56] References Cited

U.S. PATENT DOCUMENTS

| | | | |
|---|---|---|---|
| 3,415,718 | 12/1968 | Forkman et al. | 435/34 |
| 3,870,601 | 3/1975 | Warren et al. | 435/34 |
| 3,957,584 | 5/1976 | Kronish et al. | 435/34 |
| 4,808,517 | 2/1989 | Blondin et al. | 435/4 |
| 4,925,789 | 5/1990 | Edberg | 435/34 |
| 5,149,656 | 9/1992 | Bitton et al. | 435/4 |
| 5,210,022 | 5/1993 | Roth et al. | 435/34 |

FOREIGN PATENT DOCUMENTS 286367  10/1988  European Pat. Off. .

OTHER PUBLICATIONS

Feng et al., Appl. Environ. Microbiol., 43(6), 1320–9, 1982.
Boehringer Mannheim Biochemicals Catalogue, 1987/88, p. 120.
Sigma Chemical Company, Catalogue, 1983, p. 542.
Muller–Hill, B., H.V. Rickenberg, and K. Wallenfels (1964) "Specificity of the Induction of the Enzymes of theLac Operon" J. Mol. Biol 10:303–318.
Freifelder, D. (1987) "The Lactose System and the Operon Model" Molecular Biology pp. 456–473.
Mazidji, C.N., B. Koopman, G. Bitton, G. Voiland (1990) "Use of Microtox and Ceriodaphnia Bioassays in Wastewater Fractionation" Toxicity Assessment: An IOnternational Journal 5:265–277.
Kuehl, Douglas W., Gerald T. Ankley, and Lawrence P. Burkhard (1990) "Bioassay Directed Characterization of the Acute Aquatic Toxicity of a Creosote Leachate" Hazardous Waste & Hazardous Materials 7:283–291.

*Primary Examiner*—Irene Marx
*Attorney, Agent, or Firm*—Saliwanchik & Saliwanchik

[57] ABSTRACT

Described here are procedures and kits for the selective detection of toxicants in environmental samples. Specifically exemplified are procedures and kits which are used to detect heavy metals. The presence of heavy metals is detected by observing the inhibition by the toxicant of a microbially produced enzyme.

2 Claims, No Drawings

ASSAY PAD AND METHOD FOR DETERMINATION OF THE PRESENCE OF TOTAL COLIFORMS

CROSS-REFERENCE TO A RELATED APPLICATION

This application is a continuation of application Ser. No. 08/188,343, filed Jan. 27, 1994 now abandoned, which is a continuation of application Ser. No. 07/946,973, filed Sep. 17, 1992, now abandoned, which is a continuation-in-part of our application Ser. No. 07/518,686, filed May 3, 1990, now U.S. Pat. No. 5,149,656.

This invention was made with government support under NSF Grant No. CES-8619073 and NSF Grant No. BCS-9117267. The government has certain rights in this invention.

BACKGROUND OF THE INVENTION

It is well documented that a great variety of pollutants can be found throughout the environment. Pollutants may be, for example, polar and non-polar compounds, detergents, and heavy metals. The accurate identification of specific types of pollutants present in a water or soil sample facilitates the determination of what, if any, danger is present, as well as the formulation of a plan for removing the pollutant or preventing its further accumulation. Thus, the ability to quickly, easily, and accurately determine whether an environmental sample (soil, sediment, water, ashes, etc.) is contaminated with a specific toxicant can be of great importance to wastewater and water treatment plant operators, hazardous waste managers, health officials, and others who have an interest in protecting public health and the environment from toxic insult. Although sophisticated techniques for analyzing environmental samples are well known, these techniques are often costly, time consuming, and cannot be done in the field because instrumentation and extensive sample preparation are necessary. Moreover, these techniques do not indicate whether the sample is toxic to the biota.

As used herein, the term toxicants refers to compounds, elements, or other entities in an environmental sample which, alone or in combination, may be injurious to humans or other living things. As used herein, the term heavy metals refers to metals such as antimony (Sb), arsenic (As), beryllium (Be), cadmium (Cd), copper (Cu), chromium (Cr), lead (Pb), mercury (Hg), nickel (Ni), selenium (Se), silver (Ag), tellurium (Te), and zinc (Zn). Existing methods for testing environmental samples for toxicants include both chemical and biological assays. Chemical assays whereby reagents are added to a test sample are well known. Chemical assays which are performed in the field often lack selectivity and provide ambiguous results. Of course, more sophisticated chemical assays can be performed in laboratories, but the sample preparation needed and expensive instrumentation limit the utility of these procedures. Recently, more attempts have also been made to develop biological toxicity assays. For example, several microbial assays have been developed for assessing chemical toxicity. These biological assays can be based on the effects of certain toxic chemicals on microorganisms. For example, toxic chemicals in a test sample may inhibit growth, respiration, motility, viability, enzyme activity or biosynthesis, bioluminescence, photosynthesis, heat production, and ATP. However, there are many obstacles which must be overcome in order to develop a biological assay that can accurately identify the presence of toxic agents. Specifically selected microbes must be found which have the desired sensitivity for toxicants. The toxicant must not only exert some type of biological effect on the microbe but, also, that effect must be easily detectable for the assay to have any utility. Finally, the effect of toxicants must be independent from any effect caused by non-toxicants. Before the current invention, no bioassay had been developed which could selectively detect the presence of specific toxicants in a sample.

Pollutants can also be in the form of biological entities such as bacteria, viruses, and protozoa. The direct detection of pathogenic bacteria and viruses and cysts of protozoan parasites requires costly and time-consuming procedures, and well-trained labor. Therefore, more easily-monitored non-pathogenic microbes which are known to be associated with pathogenic microbes are often used as "indicator organisms" of microbial pollution. Traditional bacterial indicators used to detect fecal pollution in the environment are total coliforms, fecal coliforms, and *Escherichia coli*. Commercially available enzymatic tests such as Colilert™ and Coliquik™ detect simultaneously, in 24 hours, both total coliforms and *E. coli* in environmental samples. In both assays, total coliforms are detected by observing β-galactosidase activity, which is based on the hydrolysis of the substrate o-nitrophenyl β-D-galactopyranoside (ONPG) to the yellow nitrophenol which absorbs light at 420 nm. *E. coli* detection is based on its ability to produce an enzyme, called β-glucuronidase, which hydrolyses a fluorogenic substrate, 4-methylumbelliferone glucuronide (MUG) to a fluorescent end product which can be easily detected with a long-wave UV lamp. After 24-hour incubation, samples positive for total coliforms turn yellow, whereas *E. coli*-positive samples fluoresce under a long-wave UV illumination in the dark.

BRIEF SUMMARY OF THE INVENTION

One embodiment of the subject invention is an assay and kit for the detection of toxicants in environmental samples such as water, wastewater, soil, sediment, and ashes. Specifically exemplified herein is an assay based on the specific inhibition of the enzyme beta-galactosidase by heavy metals. One of the primary advantages of this assay is that it is very selective for heavy metals. Organic and inorganic non-metal toxicants are not detected by this assay. Therefore, it is possible to rapidly differentiate between types of toxicants which may exist within a sample.

In one preferred embodiment of the invention, a specific beta-galactosidase-producing bacterium is used to supply the enzyme. The beta-galactosidase from this bacterium is highly and specifically sensitive to heavy metal toxicity. The bacterium is freeze-dried and then reconstituted before use, in this assay. A preferred embodiment further comprises the incorporation of a beta-galactosidase substrate onto an assay pad. Advantageously, a sample can be tested by simply mixing the reconstituted bacteria with a test sample and applying a small amount of the mixture to the test pad containing the enzyme substrate. Heavy metal toxicity is identified by observing color change or fluorescence intensity on the pad.

A further aspect of the invention is a kit which facilitates rapid, convenient detection of heavy metal toxicants. This kit comprises the bacterial reagent and assay pads. The kit may further comprise a diluent and buffer. The kit may further comprise confirmatory chemicals or supplies, data logger or encoder, and battery-operated incubator.

The subject invention further pertains to materials, assays, and kits for the detection of microbiological indicator organisms in environmental samples. Specifically, a method for detecting total coliform and *E. coli* is provided. This method can advantageously utilize pads which comprise two enzyme substrates—one which is acted upon and converted to a detectable substance by β-galactosidase and the other which is acted upon and converted to a detectable substance by β-glucuronidase.

DETAILED DESCRIPTION OF THE INVENTION

In one embodiment of the subject invention, the biological assay of the subject invention selectively detects the presence of heavy metals in an environmental sample. The sample can be, for example, water, soil, sediment, or ashes and does not have to go through extensive sample preparation. The presence of heavy metals is detected by observing the effect of the sample on beta-galactosidase activity. Beta-galactosidase is an enzyme which normally catalyzes the biochemical conversion of lactose to glucose and galactose. Beta-D-galactosidase (beta-D-galactoside galactohydrolase, lactase, E.C. 3.2.1.23) is extensively used in food and milk industries, agriculture, and medicine. Sweet syrup, prepared from whey, following lactose hydrolytic action, is used to sweeten ice cream, soft drinks, and bakery products. Bacteria, yeasts, fungi, plants, and some animal organs can serve as a source of beta-galactosidase. Another commercial source of beta-galactosidase is LACTAID™, which is used for the degradation of lactose in milk for consumers suffering from beta-galactosidase deficiency. The properties (e.g., temperature and pH optima) of beta-galactosidase depend on the producing microorganism. For example, fungal lactases act at an acid range (pH= 2.5–4.5) whereas the pH optima for yeast and bacterial lactases are 6–7 and 6.5–7.5, respectively. Optimal temperatures may also vary from 35°–40° C. for *E. coli* to 70° C. for the fungus *Alternaria alternaria*. The enzyme is often produced inside the cell, but some fungal species (e.g., *Fusarium moniliforme*) produce extracellular beta-galactosidase.

Beta-D-galactosidase catalyzes the hydrolysis of lactose and other galactosides. Lactose is hydrolyzed to glucose and galactose.

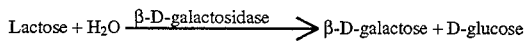

Glucose and galactose can be determined by conventional methods. Also, beta-galactosidase activity can be assayed utilizing special substrates which are converted into detectable (colored or fluorescent) compounds. For example, by using a substrate which fluoresces when it is hydrolyzed by beta-galactosidase, it is possible to assess the activity of the beta-galactosidase by measuring the release of fluorescence by the hydrolyzed substrate.

One such approach for the determination of beta-galactosidase consists of using methylumbelliferyl-beta-galactoside (MUGA) as a substrate and measuring the liberated methylumbelliferone via fluorescence. However, the most common assay for beta-galactosidase is based on the use of a synthetic chromogenic substrate, o-nitrophenyl-β-D-galactoside (ONPG). ONPG is hydrolyzed to o-nitrophenol, a yellow product which is measured spectrophotometrically at 420 nm. One enzyme unit is one micromole of nitrophenol liberated from ONPG/min.

It has been found that the presence of heavy metals inhibits beta-galactosidase activity. Therefore, in the example described above, fluorescence reduction resulting from exposure of beta-galactosidase to the test sample can be indicative of heavy metal pollution in the sample. Advantageously, it has been determined that beta-galactosidase activity is not inhibited by pollutants or toxicants other than heavy metals. Neither organic nor inorganic non-metal toxicants were found to inhibit beta-galactosidase activity. Although strong oxidants such as chlorine may slow beta-galactosidase activity, the effect of such compounds can be rapidly and conveniently eliminated by adding a reducing agent such as sodium thiosulfate. Therefore, the novel assay and kit described here provide very selective means for detecting the presence of heavy metals even when the metals are mixed with other toxicants.

The beta-galactosidase used in the assay of the subject invention can be supplied from a variety of sources. Specifically exemplified herein is beta-galactosidase which is produced by a microorganism. Certain strains of high-producers of beta-galactosidase are described.

In one preferred embodiment of the invention, the beta-galactosidase producing bacteria are freeze-dried so that they can be stored and later reconstituted for use in the assay. The freeze-drying process facilitates the shipping of the cells and also enhances the permeability of cells to toxicants, including heavy metals.

An important aspect of the subject invention is the provision of kits which facilitate the easy and accurate detection in the field of heavy metals in environmental samples. These kits comprise a source of beta-galactosidase and a substrate which is formulated and presented in such a fashion so as to enable the determination of beta-galactosidase activity. In one preferred embodiment of the novel kit, the kit comprises a pad into which an appropriate substrate has been incorporated. Such a substrate-containing pad is known as a MetPAD™ (formerly known as TOXIPAD), and the assay is known as the MetPAD™ Assay. The assay is performed by simply mixing the analytical sample with a source of beta-galactosidase. As described above, the source of beta-galactosidase may be freeze dried (and reconstituted) beta-galactosidase-producing bacteria or other microorganism. If the sample is highly toxic, several dilutions of the sample may be tested using the MetPAD™ assay and a Minimum Inhibitory Concentration (MIC) may be determined. The diluent used can be deionized, activated-carbon treated, microfiltered water such as MilliQ™. Following addition of the toxicant, a buffer may be added to ensure that the enzymatic assay is carried out under a constant pH.

A small amount of the solution with the beta-galactosidase and analytical sample is then applied to the MetPAD™. Color change or fluorescence reduction can then be easily observed as the measure of beta-galactosidase activity. A lack or a reduction of such activity identifies the presence of heavy metals in the sample.

MATERIALS AND METHODS

Characteristic Enzyme Substrates Used in MetPAD™.

One substrate which can be used according to the subject invention is chlorophenol red-beta-D-galactopyranoside (CPRG), which can be purchased from Boehringer Mannheim Inc. The solubility of CPRG is more than 50 mmol/L. It is stable at −20° C. and must be protected from light. CPRG was dissolved in 50 mM K-phosphate buffer containing 1 mM MgCl$_2$. The pH of the CPRG solution was 7.5 This solution is stable at 4° C. for one week. When the beta-galactosidase catalzyed hydrolysis of CPRG occurs, the resulting product on the MetPAD™ is purple and, thus, is easily detected visibly.

Another beta-galactosidase substrate which can be used is 4-methylumbelliferyl-beta-D-galactoside (MUGA), purchased from Sigma (Cat. #M-1633) and prepared at a concentration of 100 mg/L in 0.05M K-phosphate buffer, pH=7.5. This substrate releases fluorescent umbelliferone when hydrolysed by beta-galactosidase.

Bacteria Used.

As described above, one convenient source of beta-galactosidase is bacteria which produce this enzyme in useful amounts. Advantageously, the enzyme produced by the bacteria is readily accessible to the heavy metal and the substrate. Certain strains of E. coli have been found to function quite well in this regard. Among the bacteria investigated by the applicants are E. coli C3000, E. coli EW1b, and a mixed culture of beta-galactosidase producers isolated from wastewater. E. coli C3000 is available from the American Type Culture Collection (ATCC), 12301 Parklawn Drive, Rockville, Md. 20852 USA. The culture has been assigned the accession number ATCC 15597 by the repository. E. coli EW1b is available from the Coli Genetic Stock Culture, Yale University, New Haven, Conn. The mixed culture was obtained following inoculation of LB-lactose-SDS broth with activated sludge effluent. Although these bacteria would perform well in the assay of the subject invention, E. coli C3000 was not as sensitive to heavy metal toxicity as E. coli EW1b or the mixture of beta-galactosidase producing bacteria. Moreover, due to potential problems in maintaining a mixed culture of bacteria, E. coli EW1b is the preferred microbe. For optimal results, it was found that bacteria which produce high levels of enzyme are preferred. Advantageously, fewer bacteria cells need to be utilized when production of enzyme is high. It was found that use of fewer bacteria cells is not only economical, but also improves the performance of the assay. Production of the enzyme of interest can be enhanced by treating the bacteria with an appropriate inducer. It was discovered that beta-galactosidase production could be enhanced by treating E. coli EW1b cells with IPTG, for example.

The test bacteria were grown in Luria's Broth supplemented with 1% lactose and buffered with phosphate buffer. They were freeze-dried, using Flexy-Dry® freeze-dryer purchased from FTS Systems, Stone Ridge, N.Y.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation of Pads for Toxicity Testing

1. Optimum Enzyme Substrate Concentration Used for Soaking the Pads.

As described above, the reaction of CPRG in the presence of beta-galactosidase results in the formation of purple coloring. In order to prepare the MetPAD™ filter pads, or similar-type pads, they can be soaked in a solution comprising the substrate. With regard to optimum purple color development, we compared pads soaked in CPRG at concentrations of 100 to 400 ppm. Color development was superior in pads soaked in 400 ppm CPRG.

It was found that the optimum MUGA (fluorescence-producing substrate) concentration was 100 mg/L.

Filter pads from Gelman Sciences were soaked into a buffered solution of beta-galactosidase substrate (CPRG or MUGA). The pads were allowed to dry overnight at room temperature in the dark.

If so desired, the pads can also be soaked in a mixture of both substrates (CPRG+MUGA). Following reaction with the enzyme, these special pads can be observed under regular light (development of purple color) or under long-range UV light (development of fluorescent spots).

2. Stability of Filter Pads.

Filter pads were soaked in buffered CPRG and incubated at room temperature, at 5° C. (refrigerator temperature), and at −15° C. A mixed culture of beta-galactosidase producing bacteria was used to test the stability of the pads (i.e., positive beta-galactosidase reaction indicated by the formation of a purple color). After various time periods, drops of bacterial cultures were spotted on the CPRG pads. The development of a purple color indicated a positive reaction.

The pads were tested after up to 4 weeks of storage. All the pads displayed a positive reaction (i.e., purple color) after storage at all temperatures investigated.

Recent testing has shown that the pads are stable for more than a year when stored in a refrigerator. Therefore, pads stored in the dark are stable and can be used after several months of storage at refrigerator temperature.

EXAMPLE 2

Bacteria Used in MetPAD™

Freeze-Drying Conditions for Assay Bacteria.

It is quite convenient to use freeze-dried bacteria in toxicity assay kits. The assay bacteria can be shipped conveniently and safely to any desired location.

It has been determined that assay bacteria freeze-dried in 12% sucrose are less sensitive to heavy metal toxicity than bacteria freeze-dried in trehalose medium (sucrose and trehalose media are cryoprotectants traditionally used for freeze-drying bacteria).

In subsequent experiments, we studied the effect of the freeze-drying medium (distilled water versus trehalose medium) on bacterial sensitivity to heavy metal toxicity. Table 1 shows that assay bacteria freeze-dried in trehalose (22.4% w/v) were more sensitive to heavy metals than bacteria freeze-dried in distilled water. However, it has also been determined that bacteria freeze-dried in 22.4% (w/v) trehalose medium cannot easily be resuspended. Therefore, the concentration of trehalose (22.4% w/v) was reduced to 11.2% (w/v).

Further modifications showed that bacteria can be freeze-dried in 2% trehalose and are easily resuspended in distilled water.

Thus, the preferred concentration of trehalose in the freeze-drying medium is 1% to 15%, and 2% is optimal.

EXAMPLE 3

Use of MetPAD™ in the Specific Determination of Heavy Metal Toxicity

1. Heavy Metal Toxicity Using MetPAD™.

The toxicity of 7 heavy metals ($Cd^{2+}$, Cr (VI), $Cu^{2+}$, $Hg^{2+}$, $Pb^{2+}$, $Ni^{2+}$, and $Zn^{2+}$) commonly found in water and wastewater is displayed in Table 2. Metal toxicity is expressed as Minimum Inhibitory Concentration (MIC) or total inactivation. MetPAD™ responds to all the heavy metals tested. Cadmium was the most toxic among the metals tested.

2. Heavy Metal Toxicity: Comparison Between Fluorescent and CPRG Pads.

The sensitivity of detecting heavy metals using fluorescent pads as compared to CPRG pads was assessed. Table 3 shows that the fluorescent pads performed slightly better than CPRG pads.

3. Toxicity of Organic Toxicants Using MetPAD™.

The toxicity of nine organic compounds was tested using MetPAD™. None of these chemicals exhibited any toxicity when assayed with MetPAD™ (Table 4).

These results clearly demonstrate that the MetPAD™ test is specific for heavy metal toxicity and does not respond to organic toxicity. This important feature allows distinction between heavy metal and organic toxicity when used in conjunction with a test for general toxicity such as MICROTOX™.

TABLE 1

Effect of suspending medium on sensitivity of *E. coli* EW1b to heavy metals.

| HEAVY METAL | COLOR INTENSITY | |
|---|---|---|
| (ppm) | Distilled Water | Trehalose Medium |
| CONTROL | +++++* | **** |
| Cadmium (CdSO$_4$) | | |
| 0.3 | ++++++ | ++ |
| 0.6 | ++++ | + |
| 1.0 | +++ | – |
| 1.5 | + | – |
| Copper (CuSO$_4$.5H$_2$O) | | |
| 0.5 | +++++ | ++ |
| 0.8 | ++++ | + |
| 1.0 | ++++ | – |
| 1.5 | ++++ | – |
| Lead (Pb(NO$_3$)$_2$) | | |
| 3.0 | | +++++ |
| 5.0 | | +++ |
| 7.0 | | ++ |
| 10.0 | | + |
| 15.0 | | – |
| 20.0 | | – |
| Mercury (HgSO$_4$) | | |
| 0.5 | ++++ | +++ |
| 1.0 | ++++ | – |
| 1.5 | ++++ | – |
| 2.0 | ++++ | – |
| Zinc (ZnSO$_4$) | | |
| 0.5 | ++++ | ++++ |
| 1.0 | ++++ | ++ |
| 3.0 | +++ | – |
| 5.0 | ++ | – |
| 7.5 | + | – |
| 10.0 | – | – |

*+++++ = maximum color intensity
– = complete enzyme inactivation

TABLE 2

Heavy metal toxicity using MetPAD ™†.

| HEAVY METAL | MIC* | TOTAL INACTIVATION** |
|---|---|---|
| Cd (CdSO$_4$) | 0.2 | 1.0 |
| Cr (K$_2$Cr$_2$O$_7$) | 25.0 | 50.0 |
| Cu (CuSO$_4$.5H$_2$O) | 0.5 | 1.0 |

TABLE 2-continued

Heavy metal toxicity using MetPAD ™†.

| HEAVY METAL | MIC* | TOTAL INACTIVATION** |
|---|---|---|
| Hg (HgSO$_4$) | 0.5 | 1.0 |
| Pb (Pb(NO$_3$)$_2$) | 5.0 | 15.0 |
| Ni (NiSO$_4$.6H$_2$O) | 8.0 | 20.0 |
| Zn (ZnSO$_4$) | 0.5–1 | 3.0 |

†All concentrations in mg/L.
*Minimum Inhibitory Concentration
**Toxicant concentration which causes 100% inhibition of enzyme activity

TABLE 3

Comparison between fluorescent and CPRG pads as regards the detection of heavy metal toxicity.

| | MINIMUM INHIBITORY CONCENTRATION (MIC; mg/L) | |
|---|---|---|
| Heavy Metal | Fluorescent Pads | CPRG Pads |
| Cadmium | 0.30 | 0.30 |
| Copper | 0.25 | 0.50 |
| Mercury | 0.25 | 0.25 |
| Nickel | 5.00 | 8.00 |
| Lead | 2.50 | 5.00 |
| Zinc | 0.50 | 0.5–1.00 |
| Chromium | 25.00 | 25.00 |

TABLE 4

Toxicity testing of organic compounds using MetPAD ™.

| TOXICANT | COLOR INTENSITY |
|---|---|
| CONTROL | +++++ |
| Pentachlorophenol (400 ppm)* | +++++ |
| Phenol (3000 ppm) | +++++ |
| Hydrothol (53 ppm) | +++++ |
| Formaldehyde** (925 ppm) | +++++ |
| Chloroform (3250 ppm) | +++++ |
| Lindane (500 ppm) | +++++ |
| p-nitrophenol (110 ppm) | +++++ |
| Sodium dodecyl sulfate (3000 ppm) | +++++ |
| Sonar (Fluoridone) (400 ppm) | +++++ |

*Maximum concentration tested at which no inhibition was observed
**Formaldehyde buffered to pH = 7.0 with K-phosphate buffer

EXAMPLE 4

Use of MetPAD™ for the Determination of Heavy Metal Toxicity in Wastewater Samples Wastewater samples were taken from the collection system of the Buckman wastewater treatment plant in Jacksonville, Fla. Four out of five samples displayed toxicity when using MetPAD™. Samples EX, MC, and CP, tested at 90% concentration level, caused 100% inhibition of bacterial beta-galactosidase. The SCM sample was also toxic (approximately 60% inhibition of the bacterial enzyme), using the CPRG pads. The GM sample was not toxic to the enzyme.

The fluorescent pads gave results similar to the CPRG pads.

Testing of industrial collection systems in Gainesville, Fla. showed that one sample out of four was toxic, using MetPAD™.

EXAMPLE 5

The MetPAD™ Kit

The MetPAD™ kit comprises the following separately compartmentalized components:
   (a) an assay pad comprising at least one enzyme substrate which is converted by the enzyme into a detectable compound; and
   (b) an enzyme which is selectively inhibited by the environmental toxicant which is to be detected.

The enzyme may be in a composition comprising freeze-dried bacteria which produce the enzyme. The kit may further comprise a diluent and buffer. The diluent may be MilliQ™ or equivalent quality water. The buffer may be pH=7.5 phosphate buffer. The kit may further comprise chemicals or resins for a confirmation step, and/or a portable incubator.

A. Preparation of freeze-dried cells

1. Stock cultures of *E. coli* EW1b are stored in 40% glycerol solution at −14° C. to −20° C.
2. Fifty μL of the stock culture are inoculated into 5 ml of LB-lactose medium (Bacto-tryptone: 1%; yeast extract: 0.5%; NaCl: 1.0%; $K_2HPO_4$: 0.15%; Lactose: 1%).
3. Cells are grown overnight at 35° C. The bacterial suspension is then diluted with 20 ml of fresh medium, amended with 1 ml of 0.2% (w/v) solution of isopropyl-beta-thiogalactoside (IPTG) and then allowed to grow to absorbance $A_{550}$=0.4–0.5.
4. Cells are centrifuged at 8000 RPM for 10 minutes.
5. The pellet is resuspended in distilled water.
6. The suspension is centrifuged for 10 minutes at 8000 RPM.
7. The suspension is resuspended in 2% trehalose to obtain an absorbance of $A_{550}$=0.2–0.25 (if using the MUGA pads for enzyme assay, an absorbance of $A_{550}$=0.10 is sufficient).
8. This suspension is dispensed in 3 ml aliquots in serum bottles.
9. The cells are frozen overnight at −40° C.
10. The frozen cells are freeze-dried for 24 hours and stored at subzero or at refrigerator temperature until used. The beta-galactosidase activity of the freeze-dried cells is stable for several weeks at 4° C. Moreover, the enzyme was stable for at least 18 hours at 35° C.
11. For toxicity testing, the freeze-dried bacteria are rehydrated with 3 ml of MilliQ™ or equivalent quality water. 0.1 ml of this bacterial suspension is added to 0.9 ml of toxic sample or dilution thereof.

B. Preparation of filter pads
1. CPRG Pads
   a. Prepare a 0.1% (w/v) CPRG stock solution in 50 mM K-phosphate buffer containing 1 mM Mg (pH=7.5).
   b. Filter-sterilize the CPRG solution via passage through a 0.2 μm filter. Store in the dark at 4° C. until used.
   c. CPRG pads are prepared by soaking filter pads into 200 ppm to 400 ppm of CPRG solution (dilute stock solution into 50 mM K-phosphate buffer).
   d. Dry pads for 24 hours in the dark at room temperature.
   e. Store pads in sealed petri dishes in the refrigerator until used.
2. Fluorescent Pads
   a. Prepare a 0.1% (w/v) of methylumbelliferyl beta-D-galactoside (MUGA) stock solution 0.05M K-phosphate buffer (pH=7.5).
   b. Filter-sterilize the MUGA solution via passage through a 0.2 μm filter. Store in the dark at 4° C. until used.
   c. Fluorescent pads are prepared by soaking filter pads into 100 ppm of MUGA solution.
   d. Dry pads for 24 hours in the dark at room temperature.
   e. Store pads in sealed petri dishes in the refrigerator until used.

EXAMPLE 6

MetPAD™ Methodology

1. Freeze-dried *E. coli* EW1b (bacterial reagent) cells are rehydrated in 3.0 ml MilliQ™ or equivalent quality water (diluent). The absorbance ($A_{550}$) of the bacterial suspension is 0.20–0.25.
2. Mix suspension for 1 minute, incubate for 10 minutes at room temperature, and mix again.
3. Add 0.1 ml of the cell suspension to 0.9 ml of sample. Add 0.9 ml of MilliQ™ or equivalent quality water or other appropriate control medium to the control tube.
4. Shake the mixture and incubate at 35° C. for 90 minutes.
5. Add 0.1 ml of 0.3M K-phosphate buffer, pH=7.5 (buffer) and mix.
6. Dispense one drop of mixture on CPRG pad or MUGA pad (assay pad). Incubate for 30 minutes at 35° C. for color or fluorescence development.
7. Observe the intensity of the purple color (if CPRG pad is used) or fluorescence intensity (if MUGA pad is used).

The fluorescence of the spots on the pads is observed using a Black-Ray Lamp, model UVL-21 (UVP, Inc., San Gabriel, Calif.), which emits long range UV at 366 nm.

The intensity of purple spots on a CPRG-impregnated pad indicates the activity of beta-galactosidase and, thus, the heavy metal toxicity in a given sample.

MetPAD™ assay is performed in 9 steps as follows:
1. Add 1.0 ml of diluent to serum bottle containing the bacterial reagent.
2. Mix thoroughly for 1 minute, let stand for 10 minutes, and mix again.
3. Add 0.1 ml of bacterial suspension to 0.9 ml of sample in assay tubes.
4. Shake assay tubes for one minute.
5. Incubate for 90 minutes at 35° C.
6. Add 0.1 ml buffer and shake.
7. Dispense drops of mixtures onto assay pads.
8. Incubate for 30 minutes at 35° C.
9. Observe purple color or fluorescence intensity and compare to control.

EXAMPLE 7

The assay of the subject invention may further comprise a confirmation step whereby the presence of the toxicant of interest can be verified. For example, in the case of heavy metals, the confirmation step may comprise the addition of a chelating or precipitating agent in the environmental sample. One such reagent which could be added is TMT. Other reagents which would perform this function are well known to those skilled in the art.

An additional confirmation step could comprise passing the environmental sample or extract through a chelating or a cation exchange resin followed by testing with the MetPAD™ assay. The resin would remove any heavy metals in the sample, and the subsequent MetPAD™ assay would then be expected to give a negative result.

The MetPAD™ kit could include chemicals or resins needed for the confirmation step.

EXAMPLE 8

A further aspect of the subject invention pertains to the preservation of the assay pad via lamination between a translucent material such as plastic. This process can be combined with procedures for encoding certain relevant data onto the pad or the laminated pad. For example, a bar encoder can be used to encode data relating to the date and location of a sample and any other identifying characteristics. The information can subsequently be retrieved with a bar decoder and transmitted to a computer for entry in a program for recording results. The bar encoder may be included in a MetPAD™ kit.

EXAMPLE 9

The results obtained using the MetPAD™ procedures described above are primarily qualitative. However, our toxicity bioassay can give quantitative results by using the MetPAD™ bacterial reagent in, for example, 96-well microplates. Procedures for using these wells are widely known and used by those skilled in the art. Specifically, these procedures involve placing different dilutions of a sample in the wells of the plate. Thus, the bacterial reagent can be exposed to undiluted and multiple dilutions of a given toxic sample for about 90 minutes at about 35° C. Afterwards, the samples in the well are buffered to pH=7.5 and amended with β-galactosidase substrate (CPRG or any other appropriate substrate) and incubated for about 30 minutes at about 35° C. Enzyme activity is determined by measuring the absorbance of the 96 wells with a plate reader. $EC_{50}$ (effective concentration of sample that causes 50% inhibition of enzyme activity) values can be calculated from the absorbance readings.

In another embodiment, 96-well plates can be provided with the β-galactosidase substrate already present in the wells. For example, the wells may be coated with a CPRG solution which is allowed to dry on the wells. For best results, these plates should be protected from light.

EXAMPLE 10

ColiPAD™

Another embodiment of the subject invention enables the detection of either or both total coliform bacteria and *E. coli* in environmental samples such as water, wastewater, sludges, sediments, soils, and feces. A modified pad useful for this procedure can comprise two enzyme substrates instead of one. Those skilled in the art will appreciate that articles other than pads can be used to present the enzyme substrate to the environmental sample. Examples of the two enzyme substrates which can be used are:

(1) Chlorophenol Red-β-D-galactopyranoside (CPRG) at a concentration of about 100 mg/L. This substrate is specific for β-galactosidase and changes from yellow to purple when β-galactosidase is present in a given sample. This indicates the presence of total coliforms which produce β-galactosidase.

(2) 4-methylumbelliferone glucuronide (MUG) at a concentration of about 100 mg/L. This substrate is specific for an enzyme called β-glucuronidase, which hydrolyses the substrate to a fluorescent end product which can be easily detected with a long-wave UV lamp in the dark. This indicates the presence of *E. coli*, which characteristically produce glucuronidase.

Thus, a pad, called ColiPAD™, can be used for confirming the presence of both total coliforms and *E. coli* in an environmental sample. The following protocol is suggested:

1. Incubate the sample in glass tubes containing lauryl tryptose broth+MUG (purchased from Difco Laboratories) for about 22 hours at 35° C.

2. From each tube, dispense about 10-μL drops on the assay pad (each pad can accommodate about 12 drops). A negative control should be run for each pad. Sterile medium serves as the negative control.

3. Place pad in a small polystyrene dish (locking petri dish) and incubate at 44.5° C. for 2 hours.

4. Record results. Purple spots indicate the presence of total coliforms. When pad is examined under a long-wave UV lamp in the dark, fluorescent spots indicate the presence of *E. coli*. Sometimes, when the fluorescence of the spot is weak, one can add to the same spot a 10 μL drop of 2-amino-2-methyl-1-propanol buffer to accentuate the fluorescence seen on the pad with a long-range UV lamp.

5. Knowing the number of positive tubes, one can compute the numbers of both total coliforms and *E. coli*, using most probable number tables.

Advantages of ColiPAD™ include:

(1) ColiPAD™ is very convenient to use and is stable for at least several months when kept in the dark in a refrigerator.

(2) Colored substances such as humic acids as well as suspended solids do not interfere with the viewing of the enzymatic reactions on the assay pad.

(3) The spots (purple and fluorescent spots) on the pad can be kept for long periods of time. Furthermore, records can be kept by photocopying the purple spots on the pad with a color photocopier.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for detecting bacteria in an environmental sample, said method comprising the following steps:

(a) incubating, in an enrichment broth, an environmental sample suspected of containing coliform bacteria;

(b) contacting the incubated environmental sample with an assay pad consisting essentially of the enzyme substrates chlorophenol red-β-D-galactopyranoside and 4-methylumbelliferone glucuronide, wherein said chlorophenol red-β-D-galactopyranoside is present at a concentration of about 100 ppm and said 4-methylumbelliferone glucuronide is present at a concentration of about 100 mg/L, and wherein said substrates are converted to a reaction product by an enzyme produced by said coliform bacteria; and (c) detecting said reaction product to determine the presence of coliform bacteria by observing a change in color or fluorescence upon said assay pad.

2. An assay pad, useful for detecting the presence of coliform bacteria in an environmental sample, said pad consisting essentially of the enzyme substrates chlorophenol red-β-D-galactopyranoside and 4-methylumbelliferone glucuronide, wherein said chlorophenol red-β-D-galactopyranoside is present at a concentration of about 100 ppm and said 4-methylumbelliferone glucuronide is present at a concentration of about 100 mg/L, and wherein said enzyme substrates, when acted upon by an enzyme produced by said bacteria, are converted to a reaction product which can be detected on said pad by observing a change in color or fluorescence.

* * * * *